(12) United States Patent
Kues et al.

(10) Patent No.: US 7,185,550 B2
(45) Date of Patent: Mar. 6, 2007

(54) TIME DOMAIN RESOLVING CHEMICAL SAMPLER USING SORBENT MATERIAL

(75) Inventors: Henry A. Kues, Sykesville, MD (US); Adam K. Arabian, Louisville, KY (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/553,935

(22) PCT Filed: Jun. 17, 2004

(86) PCT No.: PCT/US2004/019402

§ 371 (c)(1),
(2), (4) Date: Oct. 20, 2005

(87) PCT Pub. No.: WO2004/113870

PCT Pub. Date: Dec. 29, 2004

(65) Prior Publication Data

US 2006/0278025 A1 Dec. 14, 2006

Related U.S. Application Data

(60) Provisional application No. 60/479,276, filed on Jun. 18, 2003.

(51) Int. Cl.
*G01N 1/22* (2006.01)

(52) U.S. Cl. .................................................. 73/863.21

(58) Field of Classification Search .................. 73/863, 73/23.2, 31.07, 863.31, 863.21
See application file for complete search history.

(56) References Cited

U.S. PATENT DOCUMENTS

| | | | |
|---|---|---|---|
| 2,699,679 A | 1/1955 | Munger | 73/863.21 |
| 3,657,864 A | 4/1972 | Davis, Jr. et al. | 96/105 |
| 3,933,431 A * | 1/1976 | Trujillo et al. | 436/76 |
| 4,182,633 A | 1/1980 | Ishikawa et al. | 127/46.2 |
| 4,584,887 A | 4/1986 | Galen | 73/863.31 |
| 5,000,052 A | 3/1991 | Sipin | 73/863.03 |
| 5,529,686 A | 6/1996 | Hagen et al. | 210/198.2 |
| 5,639,372 A | 6/1997 | Hagen et al. | 210/198.2 |
| 5,738,790 A | 4/1998 | Hagen et al. | 210/635 |
| 6,321,609 B1 | 11/2001 | Mengel et al. | 73/863.21 |
| 6,477,906 B1 | 11/2002 | Peterson | 73/863.21 |
| 2002/0014160 A1* | 2/2002 | Higashino et al. | 96/152 |

* cited by examiner

*Primary Examiner*—Hezron Williams
*Assistant Examiner*—Tamiko Bellamy
(74) *Attorney, Agent, or Firm*—Francis A. Cooch

(57) ABSTRACT

A fluid sampling device is provided comprising an elongated housing having a longitudinal axis, a plurality of alternating sorbent units and spacer units disposed longitudinally through the housing and slidably movable therethrough along the longitudinal direction, and means for individually and sequentially exposing the sorbent units to a fluid. The adsorbed components can then be desorbed and analyzed to provide composition data of target compounds in a fluid, e.g., a gas, over a period of time.

32 Claims, 4 Drawing Sheets

TIME DOMAIN RESOLVING CHEMICAL SAMPLER USING SORBENT MATERIAL

CROSS REFERENCE TO RELATED APPLICATIONS

This application claims priority to U.S. Provisional Application No. 60/479,276, filed Jun. 18, 2003, the contents of which are incorporated herein by reference.

BACKGROUND OF THE INVENTION

1. Field of the Invention

The present invention generally relates to an apparatus and method for sampling a fluid over a period of time.

2. Description of the Related Art

Devices for periodically testing a gas to provide a time domain of chemical background are known. Such devices include, for example, multiple metal or glass tubes, each tube having a sorbent material. Generally, gas is drawn through one of these tubes using a commercial pump and the results are analyzed using a commercial thermal desorber and an analysis unit such as, for example, a gas chromatograph, mass spectrometer, or pulse flame photometer.

Currently, to obtain information in the time domain, i.e., sampling measurements over a period of time to determine changes in composition, it is necessary to use a cascade of tubes and a complex set of valves or a continual manual change of values or some other extensive and/or expensive technique.

For example, U.S. Pat. No. 6,321,609 B1 discloses a gas sampling system having a removable magazine that fits within a port of a trapping module and has a rotating carousel with multiple individual sample tubes. However, when multiple sample tubes are used, the sample must be exposed to a small amount of sorbent at any given time, and when multi-bed absorbent mixtures are used, non-symmetric exposure typically occurs. All of these occur without time domain data. What is needed is the ability to have target compounds exposed to and absorbed onto a series of absorbent materials and the ability to desorb the compounds so as to retrieve composition data of target compounds and/or compositions over a period of time.

SUMMARY OF THE INVENTION

A fluid sampling device is provided herein. In accordance with the present invention, a fluid sampling device is provided comprising a housing having a longitudinal axis, a plurality of alternating sorbent units and spacer units disposed longitudinally through the housing and slidably movable therethrough along the longitudinal direction, and means for individually and sequentially exposing the sorbent units to a fluid. The adsorbed or absorbed components can then be desorbed and analyzed to provide time domain composition data of target compounds.

BRIEF DESCRIPTION OF THE DRAWINGS

Various embodiments are described below with reference to the drawings wherein.

DETAILED DESCRIPTION OF THE PREFERRED EMBODIMENTS

Figure 1:
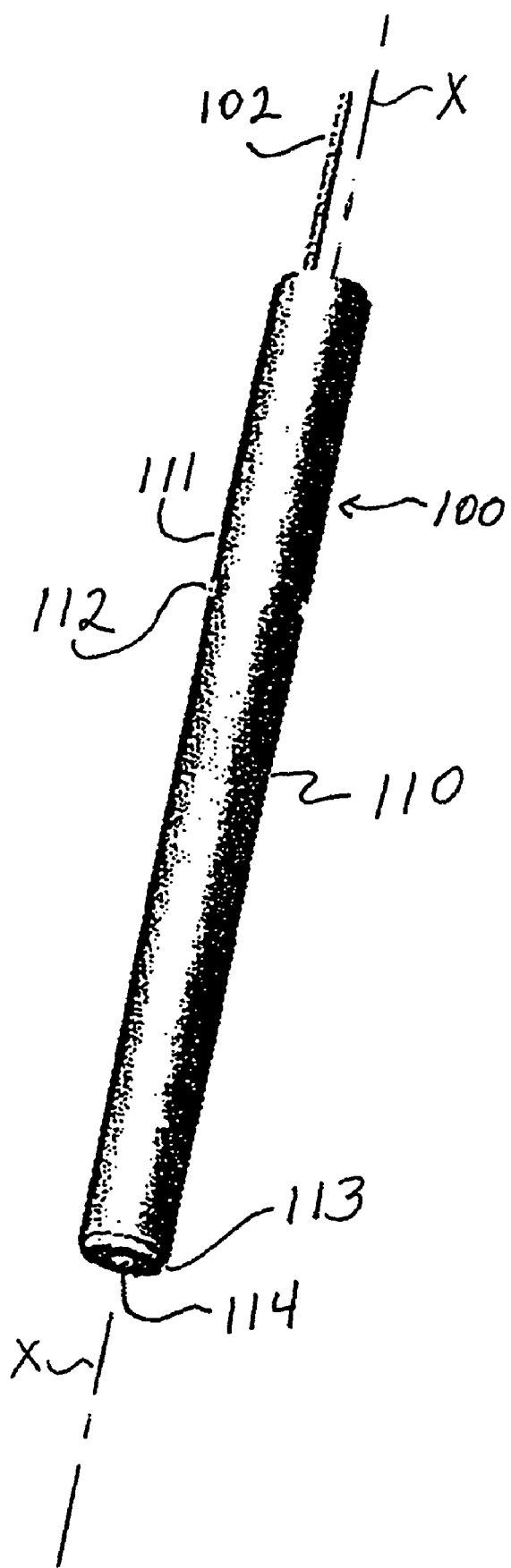
FIG. 1 is a perspective view of an apparatus of the present invention.
Figure 2:
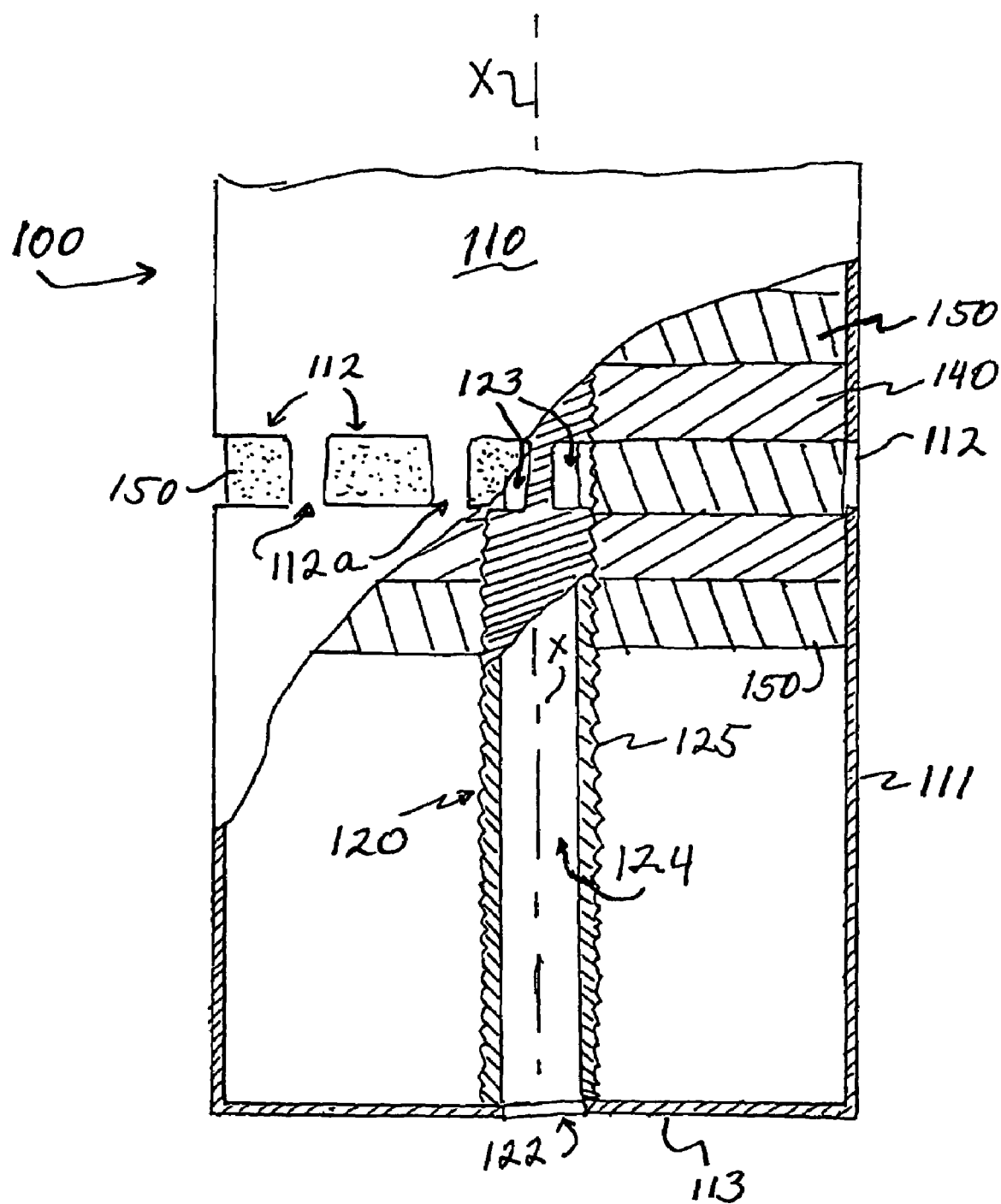
FIG. 2 is a partially cut away sectional view of the apparatus.

Referring now to FIGS. 1 and 2, in one embodiment of the fluid sampling device 100 of the present invention includes at least an elongated housing 110 having one or more fluid inlet openings 112 circumferentially disposed around a tubular wall 111. The fluid can be passed sequentially through individual sorbent units 150 at spaced intervals of time and then exit the device 100 at an outlet 114 at end 113 of the housing. Ratcheting rod 102 can provide means for advancing the stack of sorbent units and spacer units to individually and sequentially position the sorbent units 150 in alignment with the fluid inlet openings 112. The fluid can be a liquid or a gas, but the sampling device 100 is more advantageously employed for monitoring a gas to detect the presence of target compounds such as, for example, chemical or biological contaminants, volatile organic compounds (VOCs), or any compound or material component carried by the gas which is capable of being retained by a sorbent material. The fluid can be drawn through the device by any means known to one skilled in the art, e.g., by way of a vacuum applied to fluid outlet 122 of axial tube 120.

More particularly now referring to FIG. 2, in an embodiment of the present invention housing 110 includes an elongated cylindrical wall 111. At least one, but preferably a plurality of fluid inlet openings 112 defined by bridging portions 112a of housing 110 and are circumferentially disposed around wall 111 equidistant from end 113 of housing 110. A center tube 120 is rotatably mounted along the longitudinal axis X of housing 110 and terminates at end 113 of the housing. Distal opening 122 provides an outlet for the escape of fluid. Center tube 120 includes at least one and preferably two or more openings 123 which allow access of the fluid to the hollow bore 124 of center tube 120. Bore 124 allows passage of the fluid therethrough from the openings 123 to the distal opening 122. Openings 123 are aligned with openings 112 of housing 110 and are equidistant from end 113 of housing 110. Center tube 120 can include an outer threaded surface 125 which engages a corresponding threaded interior surface of sorbent units 150 and/or spacer units 140.

A plurality of alternating sorbent units 150 and spacer units 140 in stacked arrangement are disposed in the interior of housing 110. The stack is slidably movable in the longitudinal direction in response to rotation of center tube 120 so as to sequentially align individual sorbent units 150 with the fluid inlet openings 112. The spacer units 140 can be fabricated from an inert material such as, for example, a synthetic polymer, or from a metal, e.g., aluminum. Suitable synthetic polymers include, but are not limited to, polytetrafluoroethylene (e.g., TEFLON®), polyethylene, polypropylene, polyvinyl chloride, nylon and the like and combinations thereof. The thickness of the individual spacer units 140 should be greater than the diameter of the fluid inlet openings 112 and the diameter of the spacer units 140 should be equal to the inner diameter of the housing 111 to preclude a fluid from contacting more than one sorbent unit 150 at the same time.

Figure 3:
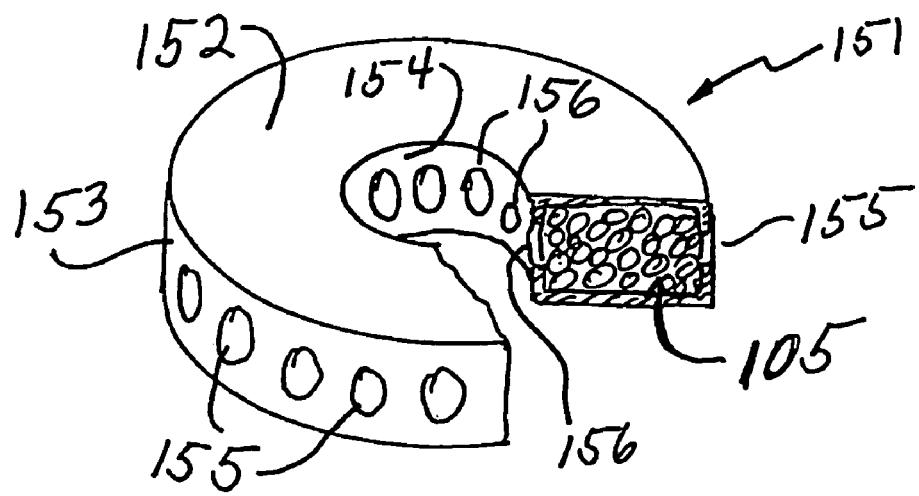
FIG. 3 is a partially cut away perspective view of an individual sorbent module.

The sorbent units 150 include at least one sorbent module 151 as generally depicted in FIG. 3. The sorbent module contains a sorbent material which can be an adsorbent or absorbent. The preferred sorbent material is an adsorbent such as, for example, activated charcoal, silica gel, soda lime, alumina/aluminum oxide or a molecular sieve from which the adsorbed component of the fluid can be desorbed by, for example, heating. However, the sorbent material can alternatively be an absorbent or any material which provides some indication of the presence and amount of a selected component in the fluid. For example, the sorbent material can change in physical or chemical properties in proportion to the amount of contaminant material. It can, for example, be a chromatic material and change color, so that the amount of a chemical contaminant can be estimated by visual inspection of the sorbent material after exposure to the gas. If desired, the composition of the sorbent material can be tailored to the specific suite of contaminants that is being monitored. Also, the composition of sorbent materials can be different one from another, especially in those circumstances wherein the presence and concentration of a variety of different contaminants is being monitored. Alternatively, the composition of sorbent materials may be the same, especially if only one, or one type of contaminant, is to be monitored. For example, if a user is monitoring ambient air for chemical contaminants having a range of activities or molecular weights, then the use of several different adsorbents as collector materials results in obtaining more complete and representative samples. On the other hand if a specific contaminant is being monitored, then use of a sorbent material that is tailored to adsorbing and trapping that particular contaminant offers advantages.

Figure 4:
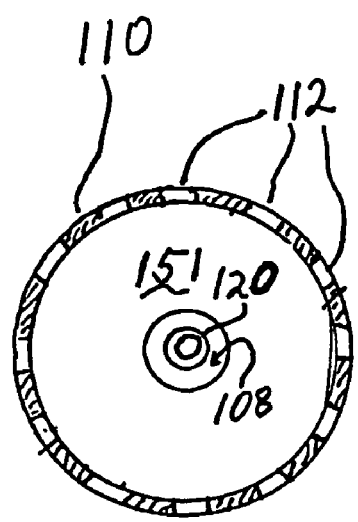
FIG. 4 is a sectional plan view illustrating the positioning of the sorbent module in the housing.

Referring now to FIGS. 3 and 4, in one embodiment, the sorbent module 151 includes an annular module housing 152 having an outer circumferential periphery 153 and an inner periphery 154 defining an axial hole. A plurality of openings 155 are disposed around the outer periphery 153 and holes 156 are disposed around the inner periphery 154. The module housing 152 encloses an interior space in which a sorbent material 105 is contained. The sorbent modules 151 are positioned in the housing 111 such that fluid enters the sorbent modules through openings 155, passes through the sorbent material 105 and then exits the sorbent module through openings 156.

The sorbent material 105 can be any suitable adsorbent such as those described above and can be in the form of particles (e.g., powder, spheres, etc.). Alternatively, the sorbent module 151 can be an integral but porous mass of sorbent material. In the event that such a mass of sorbent material has sufficient strength to be able to maintain its shape without crumbling, cracking or deforming under the stresses encountered in the operation of the device 100, a module housing is not needed.

Figure 5:
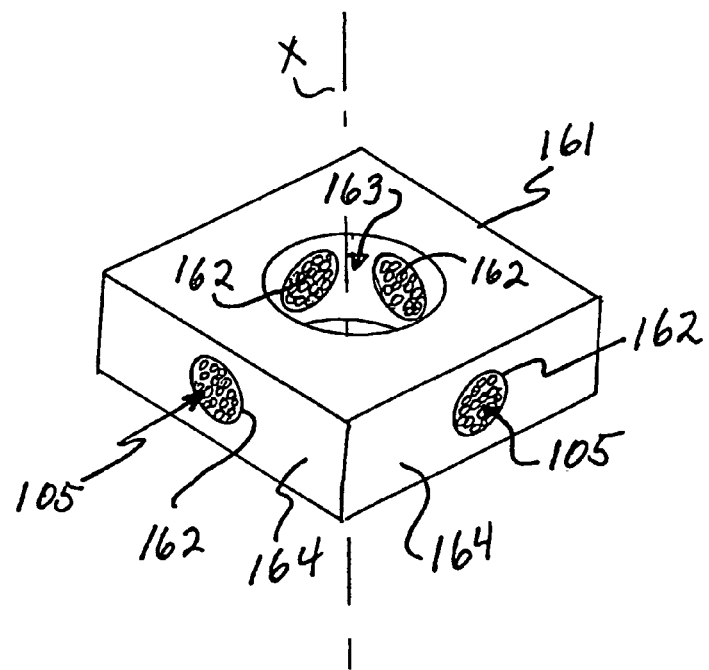
FIG. 5 is an alternative embodiment of the sorbent module having a substantially quadrangular configuration.
Figure 6:
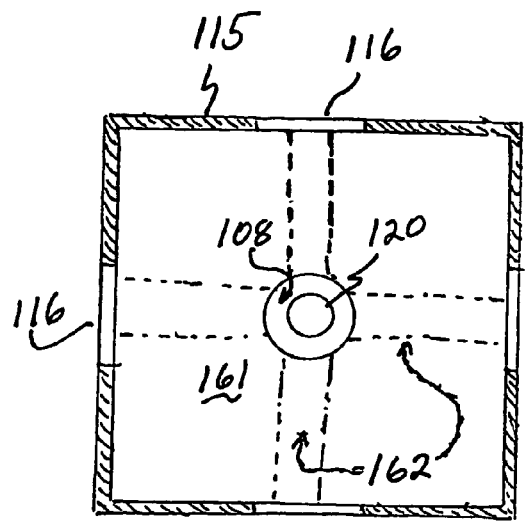
FIG. 6 is a sectional plan view of an alternative embodiment of the apparatus having a quadrangular cross section; and, FIG. 7 is a plan view of a portion of an embodiment including the apparatus illustrating a boss on the inner surface of the housing wall to facilitate longitudinal movement of the sorbent and spacer units.

Referring now to FIGS. 5 and 6, an alternative embodiment is generally depicted. Sorbent module 161 has a substantially quadrangular, preferably square, configuration with an axial opening 163. Channels 162 in the body of the sorbent module 161 extend from the exterior periphery 164 to the axial opening 163. The channels 162 contain a sorbent material 105.

The housing 115 also has a substantially quadrangular configuration and possesses inlet opening 116 to permit entry of a fluid. A plurality of modules 161 and spacers (not shown) are stacked in an alternating relationship and are movably disposed within the interior of housing 115 such that an individual sorbent module 161 can be positioned in alignment with the openings 116. The fluid is drawn into the housing through inlet openings 116, then through the sorbent-filled channels 162 of the sorbent module, and into exit passageway 108 for eventual discharge.

Figure 7:
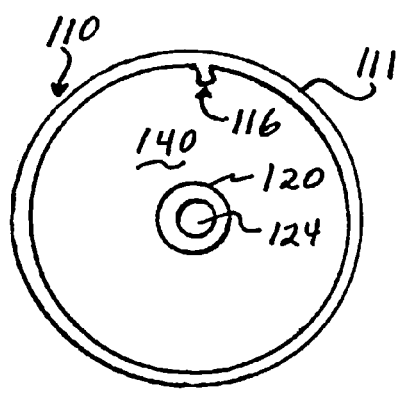

In operation, the device 100 is exposed to an environment containing the fluid. The stack of sorbent units and spacer units is advanced until a first sorbent unit is aligned with the inlet openings on the wall of the housing. Various mechanisms for moving the stack are within the purview of those with skill in the art such as, for example, rack and pinion mechanism, ratcheting mechanisms, screw mechanisms, gears, and the like. For example, referring to FIGS. 2 and 7, in a cylindrical embodiment of the present invention the housing includes an inwardly projecting ridge or boss, 116. Spacers 140 and sorbent units 150 have a corresponding groove in which boss 116 is engaged when the spacers and sorbent units are disposed in the housing. The boss prevents the stack from rotating. Therefore, as center tube 120 is rotated, the stack of spacers and sorbent units will move longitudinally through housing 110. Alternatively, use of a threaded top plate and bottom plate at the ends of the stack of spacer units and sorbent units would preclude the need to have the stack threaded to engage the center tube.

In yet another embodiment, a rack-and-pinion mechanism can be used wherein a second rod aligned with the longitudinal axis and offset from the primary central tube has sequential indentations which engage with a pinion gear located on the top of the entire assembly. The pinion gear could be used to forcefully drive the stack of sorbent unit and spacers which are rigidly attached to center tube 120 by, for example, clips, cuffs, screws, etc., or it could be used to simply restrain motion, with the primary motive force for the sorbent units spacers being a compression spring located in the bottom of the full assembly or a tension spring located in the top.

In yet another embodiment, a ratcheting mechanism can be used which includes an interface with an alternating mechanism akin to the hand on a mechanical clock. The advancement of the stack of spacers and sorbent units would be achieved by rotating the hand through a small range of motion either once, should the engaging surface be very coarsely grooved, or numerous times as seen in a mechanical clock. The ratcheting mechanism could either be the primary motive force, or it could be used to restrain the system from advancement when the primary force is provided by a compression spring in the bottom of the assembly or a tension spring located in the top.

A vacuum can be applied to opening 122 at end 113 of device 100 so as to draw the fluid in through inlet openings 112. The fluid circulates through center tube 120 and is drawn through the sorbent module(s) 151 for a predetermined period of exposure time. The fluid, upon passing through the sorbent module 151, then enters longitudinal passageway 108. Subsequently, the fluid enters holes 121 in the central tube and is then discharged through opening 122.

After the exposure time is elapsed, the stack is advanced either to move spacer unit 140 into alignment with fluid inlet 112 so as to halt monitoring of the fluid for a period of time, or to move the next sorbent unit into alignment with fluid inlet openings 112. The procedure is then repeated until the desired number of sorbent units have been sequentially contacted with the fluid over a period of time.

The sorbent units can then be desorbed prior to analysis. For analysis, an analytical instrument such as, for example, a gas chromatograph, can be connected to outlet 122. In one embodiment to facilitate desorption, the device is heated and then pure inert carrier gas such as dry nitrogen is drawn through the sorbent units individually and sequentially to desorb the adsorbed components. Alternatively, the sorbent units can be individually separated from the device prior to desorption such that the individual modules are heated and then exposed to the carrier gas. In another embodiment, desorption is accomplished by a solvent extraction technique. In this technique, the sorbent units are exposed to a solvent, e.g., halogenated hydrocarbon solvents, e.g., methylene chloride; alcohols, e.g., methanol or isopropanol; and ethyl acetate, by way of, for example, immersion, to facilitate desorption. The analytical instrument can then provide composition data for the monitored fluid over the period of sampling time.

The device 100 provides the ability to have target compounds such as contaminants, e.g., volatile organic compounds, exposed to and absorbed onto a series of sorbent materials and the ability to desorb the compound, thereby providing a time resolution of contaminant amounts that is not available in current technologies. Moreover, the device 100 provides the ability to have contaminants exposed to and absorbed onto a number of different sorbent materials at the same time, and the ability to desorb the contaminants in a like fashion, thus providing the ability to tailor collections to specific target substances that is not available in current technologies.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A fluid sampling device comprising:
a) a housing having a longitudinal axis;
b) a plurality of alternating sorbent units and spacer units disposed longitudinally through said housing and slidably movable therethrough along the longitudinal direction; and,
c) means for individually and sequentially exposing said sorbent units to the fluid.

2. The device of claim 1, wherein the sorbent units and spacer units each have an annular disk shape with an axial aperture and a respective thickness, the alternating sorbent units and spacer units being in a stacked arrangement wherein the respective axial apertures are aligned with the longitudinal axis of the housing.

3. The device of claim 2, further comprising a tube extending along the axis of the housing.

4. The device of claim 3, wherein the outer surface of the tube is threaded.

5. The device of claim 4, wherein the sorbent units and/or spacer units are in threaded engagement with the tube.

6. The device of claim 3, wherein the housing has at least one fluid inlet aperture positioned along a side of the housing and a fluid outlet disposed at an end of the housing in alignment with the axis of the housing.

7. The device of claim 6, wherein the tube has a hollow bore and at least one opening permitting fluid passage into the hollow bore, the at least one opening being aligned with the fluid inlet aperatures positioned along the side of the housing, the opening in the tube and fluid inlet aperatures being equidistant from the end of the housing.

8. The device of claim 6, wherein the fluid inlet has a diameter no larger than the thickness of the individual spacer units.

9. The device of claim 2, wherein the sorbent units have a diameter less than that of the spacer units.

10. The device of claim 2, wherein the sorbent unit comprises one or more sorbent modules, each sorbent module comprising one or more sorbent material.

11. The device of claim 10, wherein the sorbent module comprises an annular disk shaped module housing having an outer circumferential surface and an inner peripheral surface defining the axial aperture, said outer circumferential surface and inner peripheral surface having a plurality of openings, wherein said module housing encloses an annular interior space containing the sorbent material.

12. The device of claim 2, wherein the sorbent unit comprises one or more sorbent modules, each sorbent module comprising at least two different sorbent material.

13. The device of claim 10, wherein the sorbent module comprises a solid porous body of the sorbent material.

14. The device of claim 3, wherein the sorbent unit comprises one or more sorbent modules, each sorbent module comprising at least two different sorbent material.

15. The device of claim 1, wherein the housing has a substantially circular cross section.

16. The device of claim 1, wherein the housing has a substantially quadrangular cross section.

17. The device of claim 14, wherein the outer surface of the tube is threaded and wherein the sorbent units and/or spacer units are in threaded engagement with the tube.

18. The device of claim 1, wherein the housing is fabricated from metal, glass, or a synthetic polymer.

19. A method for sequential sampling a fluid over a period of time comprising:
(a) providing a fluid sampling device comprising:
  (i) a housing having a longitudinal axis, the housing having at least one fluid inlet aperture positioned on the side of the housing and a fluid outlet positioned at an end of the housing; and,
  (ii) a plurality of alternating sorbent units and spacer units disposed longitudinally through the housing in a stacked arrangement and slidably movable therethrough along the longitudinal direction;
(b) sequentially aligning individual sorbent units with the fluid inlet aperture, admitting a fluid through the fluid inlet aperture and moving the fluid through the aligned sorbent unit for a predetermined period of sampling time, then moving the stack of sorbent units and spacer units longitudinally through the housing to position a following individual sorbent unit into alignment with the fluid inlet aperture;
(c) desorbing adsorbed compounds in the fluid from the predetermined individual sorbent units; and,
(d) analyzing the desorbed compounds.

20. The method of claim 19, wherein the step of admitting fluid through the fluid inlet aperture comprises applying a vacuum to the fluid outlet.

21. The method of claim 19, wherein the step of desorbing the adsorbed compounds comprises heating the sorbent units.

22. The method of claim 21, wherein the step of desorbing the adsorbed compounds further comprises passing an inert gas through the heated sorbent units in a sequential manner.

23. The method of claim 19, wherein the step of desorbing the adsorbed compounds comprises separating the sorbent units from the device and heating the individual sorbent units to facilitate desorption.

24. The method of claim 23, wherein the step of desorbing the adsorbed compounds further comprises passing an inert gas through the individual heated sorbent units.

25. The method of claim 19, wherein in the step of analyzing the desorbed compounds comprises gas chromatography, mass spectoscopy or pulse flame photometry.

26. The method of claim 23, wherein in the step of analyzing the desorbed compounds comprises gas chromatography, mass spectoscopy or pulse flame photometry.

27. The method of claim 19, wherein the device further comprises a tube extending along the axis of the housing.

28. The method of claim 27, wherein the tube is threaded.

29. The method of claim 28 wherein the sorbent units and/or spacer units are in threaded engagement with the tube.

30. The method of claim 19, wherein the housing of the device has a substantially quadrangular cross section.

31. The method of claim 19, wherein the sorbent units of the device comprises one or more sorbent modules, each sorbent module comprising at least two different sorbent material.

32. The method of claim 19, wherein the sorbent units of the device comprises one or more sorbent modules, each sorbent module comprising one or more sorbent material.

* * * * *